United States Patent [19]

Stähler et al.

[11] Patent Number: 4,564,611
[45] Date of Patent: Jan. 14, 1986

[54] (DI)THIO-PHOSPHORIC AND -PHOSPHONIC ACID DERIVATIVES, AND THEIR USE IN PLANT PROTECTION

[75] Inventors: Gerhard Stähler, Frankfurt am Main; Werner Knauf, Eppstein/Taunus; Burkhard Sachse, Kelkheim; Anna Waltersdorfer, Frankfurt am Main, all of Fed. Rep. of Germany

[73] Assignee: Hoechst Aktiengesellschaft, Frankfurt (Main), Fed. Rep. of Germany

[21] Appl. No.: 518,295

[22] Filed: Jul. 28, 1983

[30] Foreign Application Priority Data

Jul. 31, 1982 [DE] Fed. Rep. of Germany ....... 3228631

[51] Int. Cl.[4] .................... A01N 57/20; A01N 57/24; C07F 9/165; C07F 9/40
[52] U.S. Cl. .................................. 514/99; 260/923; 514/114; 549/218
[58] Field of Search ........................ 260/923; 424/211; 549/218; 514/99, 114

[56] References Cited

U.S. PATENT DOCUMENTS 3,518,327  6/1970  Fearing ................................ 260/923
3,705,928 12/1972  Stolzer et al. ....................... 260/923

Primary Examiner—Anton H. Sutto
Attorney, Agent, or Firm—Curtis, Morris & Safford

[57] ABSTRACT

Compounds of the formula I

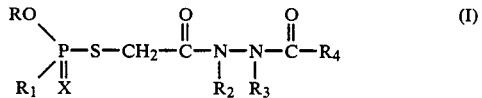

in which R denotes alkyl, $R_1$ denotes alkyl, alkoxy, alkylmercapto, alkylamino or dialkylamino, $R_2$ and $R_3$ independently of one another denote H, alkyl, cycloalkyl, benzyl or furylmethyl, $R_4$ denotes alkyl, alkoxymethyl, alkylmercaptomethyl or phenyl and X denotes oxygen or sulfur, have valuable insecticidal, acaricidal and nematocidal properties.

10 Claims, No Drawings

(DI)THIO-PHOSPHORIC AND -PHOSPHONIC ACID DERIVATIVES, AND THEIR USE IN PLANT PROTECTION

The present invention relates to new (di)thiophosphoric and -phosphonic acid derivatives of the formula (I)

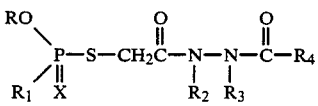 (I)

in which
R denotes $(C_1-C_4)$-alkyl,
$R_1$ denotes $(C_1-C_4)$-alkyl, $(C_1-C_4)$-alkoxy, $(C_1-C_4)$-alkylmercapto, $(C_1-C_4)$-alkylamino or di$(C_1-C_4$-alkyl)-amino,
$R_2$ and $R_3$ independently of one another denote H, $(C_1-C_4)$-alkyl, $(C_5-C_6)$-cycloalkyl, benzyl or furylmethyl,
$R_4$ denotes $(C_1-C_4)$-alkyl, $(C_1-C_3)$-alkoxymethyl, $(C_1-C_3)$-alkylmercaptomethyl or phenyl and X denotes oxygen or sulfur.

Preferred compounds of the formula I are those in which $R_1$ denotes $(C_1-C_4)$-alkylamino or di$(C_1-C_4$-alkyl)-amino and $R_2$ and $R_4$ denote $(C_1-C_4)$-alkyl.

Particularly preferred compounds of the formula I are those in which $R_1$ denotes $(C_1-C_4)$-alkylamino, $R_2$ denotes $(C_1-C_4)$-alkyl, $R_3$ denotes hydrogen and $R_4$ denotes methyl.

The present invention also relates to a process for the preparation of compounds of the formula I, which comprises reacting compounds of the formula II

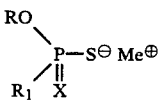 (II)

in which R, $R_1$ and X have the meanings given for formula I and $Me^\oplus$ denotes an alkali metal cation, in particular a sodium or potassium ion, or an ammonium ion, with a compound of the formula III

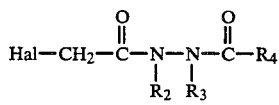 (III)

in which $R_2$, $R_3$ and $R_4$ have the meanings given for formula I and Hal represents halogen, preferably chlorine or bromine.

The reaction is in general carried out in the presence of inert solvents, such as, for example, lower aliphatic alcohols, such as methanol or ethanol, ketones, such as acetone or methyl ethyl ketone, lower nitriles, such as acetonitrile, aromatics, such as toluene, xylene or chlorobenzene, or water at temperatures between room temperature and the boiling point of the solvent used, preferably between 40° and 100° C.

The compounds are obtained as viscous resins or viscous, non-distillable oils, which can be purified by chromatography.

The compounds of the formula III can be prepared by reacting compounds of the formula IV

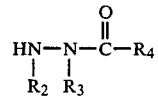 (IV)

in which $R_2$, $R_3$ and $R_4$ have the abovementioned meanings, and which can be prepared, for example, analogously to the process described in German Pat. No. 1,003,215, with halogenoacetyl chlorides of the formula V

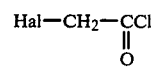 (V)

in which Hal has the meaning given for formula III, in the presence of organic bases, such as, for example, tertiary organic nitrogen bases, in particular pyridine or triethylamine, in inert solvents.

The compounds of the formula I according to the invention have an excellent action against sucking and biting insects, against acarides and against nematodes. In addition, they are also effective against pests of stored products and against species from the group of hygiene pests. When used against insects, mites and nematodes which are harmful to plants, the compounds of the formula I are also distinguished by their good tolerance to plants and by systemic properties, in addition to their contact action and ingested poison action.

Thus, various species of spider mites, such as the fruit tree red spider mite (*Panonychus ulmi*), the citrus red spider mite (*Panonychus citri*) and the two-spotted spider mite (*Tetranychus urticae*) can readily be combated.

The harmful insects which have sucking and biting mouth-parts and can be combated with the compounds according to the invention include; beetles, such as the Mexican bean beetle (*Epilachna varivestis*), Colorado beetle (*Leptinotarsa decemlineata*), species of flea beetles (*Phyllotreta spp.*), strawberry rhynchites (*Coenorrhinus germanicus*), strawberry blossom weevil (*Anthonomus rubi*), cotton boll weevil (*Anthonomus grandis*) and dart moths (*Agriotes spp.*); butterflies and their larvae, such as the Egyptian and old-world bollworm (*Earias insulana* and *Heliothis armigera*) and tobacco budworm (*Heliothis virescens*), moths, in particular the codling moth (*Carpocapsa pomonella*), oak roller moth (*Tortrix viridana*), summer fruit tortrix moth (*Adoxophyes reticulana*), bud moth (*Hedya nubiferana*), grape berry moth (*Eupoecilia ambiguella*), cornmoth (*Ostrinia nubilalis*), cutworms (*Agrotis spp.*), winter moth (*Operopthera brumata*) and nun moth (*Lymantria monacha*); and also flies, such as the mangold fly (*Pegmoya betae*) and Mediterranean fruit fly (*Ceratitis capitata*) and cockroaches, such as the German cockroach (*Blatta germanica*) and Oriental cockroach (*Blatta orientalis*) as well as aphids, such as the black bean aphid (*Doralis fabae*), peach-potato aphid (*Myzus persicae*) and melon and cotton aphid (*Aphis gossypii*), and bugs, for example cotton bugs (*Oncopeltus fasciatus* and *Dysdercus spp.*). The compounds of the formula I are active against all or individual development stages of normally sensitive and resistant species.

The compounds of the formula I also have an excellent action against nematodes which are harmful to plants, for example those of the genera Meloidogyne, Heterodera, Ditylenchus and Aphelenchoides.

The claimed compounds of the formula I furthermore display a good fungicidal, and in some cases systemic, action against phytopathogenic fungi. The compounds attack, for example, *Phytophthora infestans, Plasmopara viticola, Phthium ultimum, Venturia inaequalis, Cercospora beticola,* powdery mildew fungi, *Piricularia oryzae* and rust fungi, and, in particular, *Rhizoctonia solani.*

The invention also relates to insecticidal, acaricidal, nematocidal and fungicidal agents, characterized in that they contain compounds of the formula I, in addition to the customary formulation auxiliaries and inert substances, and to the use of the compounds for combating phtyopathogenic fungi, harmful insects, nematodes which damage plants, and acarides.

The agents according to the invention in general contain the active compounds of the formula I to the extent of 1–95% by weight. They can be used as wettable powders, emulsifiable concentrates, sprayable solutions, dusting agents or granules in the customary formulations.

Wettable powders are products which can be uniformly dispersed in water and, in addition to the active compound, and as well as a diluent or inert substance, also contain wetting agents, for example polyoxyethylated alkylphenols, polyoxyethylated fatty alcohols and alkyl- or alkylphenol-sulfonates, and dispersing agents, for example sodium lignin-sulfonate, sodium 2,2'-dinaphthylmethane-6,6'-disulfonate, sodium dibutylnaphthalenesulfonate or sodium oleylmethyl-taurate.

Emulsifiable concentrates are prepared by dissolving the active compound in an organic solvent, for example butanol, cyclohexanone, dimethylformamide, xylene or higher-boiling aromatics or hydrocarbons, with the addition of one or more emulsifiers. Examples of emulsifiers which can be used are: calcium alkylarylsulfonates, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters and polyoxyethylene sorbitol esters.

Dusts are obtained by grinding the active compound with finely divided solid substances, for example talc or natural clays, such as kaolin, bentonite, poryphillite or diatomaceous earth. Granules can be prepared either by atomizing the active compound onto an adsorbent, granular inert material or by applying active compound concentrates to the surface of carrier materials, such as sand or kaolinite, or a granular inert material by means of tackifying agents, for example polyvinyl alcohol, sodium polyacrylate or mineral oils. Suitable active compounds can also be formulated in the manner customary for the preparation of fertilizer granules—if desired as a mixture with fertilizers.

The active compound concentration in wettable powders varies, for example, between about 10% and 80%, the remainder consisting of the abovementioned formulation additives. In emulsifiable concentrates, the active compound concentration can also be about 10% to 80%. Dust-like formulations usually contain 5–20% of active compound, and sprayable solutions about 2–20%. In the case of granules, the active compound content partly depends on whether the active compound is liquid or solid and the granulating auxiliaries, fillers and the like used.

For application, the commercially available concentrates are diluted, if appropriate, in the customary manner, for example by means of water in the case of wettable powders and emulsifiable concentrates. Suspensions ready for spraying preferably contain 0.05 to 2%, in particular 0.1 to 1%, of active compound. Dust-like and granular formulations and sprayable solutions are not diluted further with other inert substances before application. The amount of agents according to the invention applied can vary between 2 g and 20 kg of active compound/ha.

The examples which follow are intended to illustrate the invention in more detail:

(A) PREPARATION EXAMPLES

Example 1

N-(O-Methyl-N-isopropylamidothiolophosphorylacetyl)-N-methyl-N'-acetylhydrazine

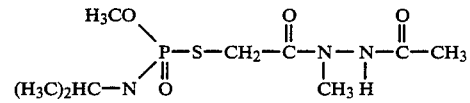

A solution of 18 g of potassium O-methyl-N-isopropylamido-thiophosphate and 14 g of N-chloroacetyl-N-methyl-N'-acetylhydrazine in 150 ml of acetonitrile is heated to the boiling point for 10 minutes. The solvent is distilled off in vacuo. The salt-containing residue is taken up in 100 ml of methylene chloride, extracted by stirring with 50 ml of water and precipitated. After the solvent has been distilled off from the organic phase, 24 g of N-(O-methyl-N-isopropylamido-thiolophosphorylacetyl)-N-methyl-N'-acetylhydrazine remain as a brownish viscous resin with the following analytical data found: N 13.8%; S 10.9% calculated: N 14.1%; S 10.8%.

Examples 2–97

The compounds listed in the table which follows were prepared in an analogous manner; in this table, the radicals R, $R_1$–$R_4$ and X relate to formula I.

| Example No. | R | $R_1$ | $R_2$ | $R_3$ | $R_4$ | X | Analysis found | calculated |
|---|---|---|---|---|---|---|---|---|
| 2 | $C_2H_5$— | $CH_3NH$— | $CH_3$ | H | $CH_3$— | O | 14.6% N<br>11.0% S | 14.8% N<br>11.3% S |
| 3 | $C_2H_5$— | $C_2H_3NH$— | $CH_3$ | H | $CH_3$— | O | 13.7% N<br>10.6% S | 14.1% N<br>10.8% S |
| 4 | $C_2H_5$— | $n$-$C_3H_7NH$— | $CH_3$ | H | $CH_3$— | O | 13.2% N<br>10.4% S | 13.5% N<br>10.3% S |
| 5 | $C_2H_5$— | $n$-$C_4H_9NH$— | $CH_3$ | H | $CH_3$— | O | 12.6% N<br>10.1% S | 12.9% N<br>9.9% S |
| 6 | $C_2H_5$— | $i$-$C_4H_9NH$— | $CH_3$ | H | $CH_3$— | O | 12.5% N<br>9.6% S | 12.9% N<br>9.9% S |
| 7 | $CH_3$— | $i$-$C_3H_7NH$— | H | $CH_3$— | $CH_3$— | O | 13.7% N | 14.1% N |

-continued

| Example No. | R | $R_1$ | $R_2$ | $R_3$ | $R_4$ | X | Analysis found | calculated |
|---|---|---|---|---|---|---|---|---|
| 8 | $C_2H_5-$ | $C_2H_5NH-$ | H | $CH_3-$ | $CH_3-$ | O | 10.9% S<br>13.8% N | 10.8% S<br>14.1% N |
| 9 | $C_2H_5-$ | $i-C_4H_9NH-$ | H | $CH_3-$ | $CH_3-$ | O | 10.5% S<br>12.5% N | 10.8% S<br>12.9% N |
| 10 | $C_2H_5-$ | $n-C_4H_9NH-$ | H | $CH_3-$ | $CH_3-$ | O | 9.7% S<br>12.4% N | 9.9% S<br>12.9% N |
| 11 | $C_2H_5-$ | $C_2H_5O-$ | H | $CH_3-$ | $CH_3-$ | S | 9.5% S<br>8.6% N | 9.9% S<br>8.9% N |
| 12 | $C_2H_5-$ | $n-C_3H_7S-$ | H | $CH_3-$ | $CH_3-$ | O | 20.1% S<br>8.2% N | 20.4% S<br>8.5% N |
| 13 | $C_2H_5-$ | $n-C_3H_7NH-$ | $C_2H_5-$ | H | $CH_3-$ | O | 9.6% S<br>12.5% N | 9.8% S<br>12.9% N |
| 14 | $C_2H_5-$ | $CH_3NH-$ | $C_2H_5-$ | H | $CH_3-$ | O | 9.6% S<br>14.0% N | 9.9% S<br>14.1% N |
| 15 | $C_2H_5-$ | $C_2H_3-NH-$ | $C_2H_5-$ | H | $CH_3-$ | O | 11.0% S<br>13.1% N | 10.8% S<br>13.5% N |
| 16 | $C_2H_5-$ | $n-C_4H_9NH-$ | $C_2H_5-$ | H | $CH_3-$ | O | 10.0% S<br>12.4% N | 10.3% S<br>12.4% N |
| 17 | $C_2H_5-$ | $n-C_3H_7S-$ | $C_2H_5-$ | H | $CH_3-$ | O | 9.6% S<br>8.2% N | 9.4% S<br>8.2% N |
| 18 | $CH_3-$ | $i-C_3H_7NH-$ | $n-C_3H_7-$ | H | $CH_3-$ | O | 18.5% S<br>12.6% N | 18.7% S<br>12.9% N |
| 19 | $C_2H_5-$ | $i-C_3H_7NH-$ | $n-C_3H_7-$ | H | $CH_3-$ | O | 10.1% S<br>12.0% N | 9.9% S<br>12.4% N |
| 20 | $C_2H_5-$ | $C_2H_5NH-$ | $n-C_3H_7-$ | H | $CH_3-$ | O | 9.2% N<br>12.6% N | 9.4% N<br>12.9% N |
| 21 | $C_2H_5-$ | $i-C_3H_7NH-$ | $n-C_3H_7-$ | H | $CH_3-$ | O | 9.6% S<br>12.1% N | 9.9% S<br>11.9% N |
| 22 | $C_2H_5-$ | $n-C_3H_7NH-$ | $n-C_3H_7-$ | H | $CH_3-$ | O | 8.8% S<br>12.8% N | 9.1% S<br>12.4% N |
| 23 | $C_2H_5-$ | $n-C_4H_9NH-$ | $n-C_3H_7-$ | H | $CH_3-$ | O | 9.0% S<br>12.4% N | 9.4% S<br>12.4% N |
| 24 | $C_2H_5-$ | $n-C_3H_7S-$ | $n-C_2H_7-$ | H | $CH_3-$ | O | 9.2% S<br>7.8% N | 9.4% S<br>7.9% N |
| 25 | $C_2H_5-$ | $C_2H_5O-$ | $n-C_2H_7-$ | H | $CH_3-$ | O | 18.1% S<br>8.5% N | 18.0% S<br>8.6% N |
| 26 | $CH_3-$ | $i-C_3H_7NH-$ | $i-C_3H_7-$ | H | $CH_3-$ | O | 10.0% S<br>12.6% N | 9.8% S<br>12.9% N |
| 27 | $C_2H_5-$ | $CH_3NH-$ | $i-C_3H_7-$ | H | $CH_3-$ | O | 10.1% S<br>13.2% N | 9.9% S<br>13.5% N |
| 28 | $C_2H_5-$ | $C_2H_5NH-$ | $i-C_3H_7-$ | H | $CH_3$ | O | 10.5% S<br>12.8% N | 10.3% S<br>12.9% N |
| 29 | $C_2H_5-$ | $n-C_3H_7NH-$ | $i-C_3H_7-$ | H | $CH_3$ | O | 9.6% S<br>12.5% N | 9.9% S<br>12.4% N |
| 30 | $C_2H_5-$ | $i-C_3H_7NH-$ | $i-C_3H_7-$ | H | $CH_3$ | O | 9.6% S<br>12.0% N | 9.4% S<br>12.4% N |
| 31 | $C_2H_5-$ | $i-C_4H_9NH-$ | $i-C_3H_7-$ | H | $CH_3$ | O | 9.2% S<br>11.6% N | 9.4% S<br>11.0% N |
| 32 | $C_2H_5-$ | $n-C_4H_9NH-$ | $i-C_3H_7-$ | H | $CH_3$ | O | 8.9% S<br>11.6% N | 9.1% S<br>11.9% N |
| 33 | $C_2H_5-$ | $C_2H_5O-$ | $i-C_3H_7-$ | H | $CH_3$ | O | 8.8% S<br>8.6% N | 9.1% S<br>8.6% N |
| 34 | $C_2H_5-$ | $C_2H_5-$ | $i-C_3H_7-$ | H | $CH_3$ | S | 9.7% S<br>8.8% N | 9.8% S<br>8.6% N |
| 35 | $CH_3-$ | $i-C_3H_7NH-$ | $n-C_4H_9-$ | H | $CH_3$ | O | 19.5% S<br>12.0% N | 19.7% S<br>12.4% N |
| 36 | $C_2H_5-$ | $CH_3NH-$ | $n-C_4H_9-$ | H | $CH_3$ | O | 9.1% S<br>12.5% N | 9.4% S<br>12.9% N |
| 37 | $C_2H_5-$ | $C_2H_5NH-$ | $n-C_4H_9-$ | H | $CH_3$ | O | 10.2% S<br>11.9% N | 9.9% S<br>12.4% N |
| 38 | $C_2H_5-$ | $n-C_3H_7NH-$ | $n-C_4H_9-$ | H | $CH_3$ | O | 9.5% S<br>11.5% N | 9.4% S<br>11.9% N |
| 39 | $C_2H_5-$ | $i-C_4H_9NH-$ | $n-C_4H_9-$ | H | $CH_3$ | O | 9.4% S<br>11.4% N | 9.1% S<br>11.4% N |
| 40 | $C_2H_5-$ | $C_2H_5O-$ | $n-C_4H_9-$ | H | $CH_3$ | S | 8.5% S<br>7.5% N | 8.7% S<br>7.9% N |
| 41 | $C_2H_5-$ | $n-C_3H_7S-$ | $n-C_4H_9-$ | H | $CH_3$ | O | 18.2% S<br>7.8% N | 18.0% S<br>7.6% N |
| 42 | $C_2H_5-$ | $n-C_3H_7NH-$ | $i-C_4H_9-$ | H | $CH_3-$ | O | 17.4% S<br>11.6% N | 17.3% S<br>11.9% N |
| 43 | $C_2H_6-$ | $n-C_4H_9NH-$ | $i-C_4H_9-$ | H | $CH_3-$ | O | 9.3% S<br>11.2% N | 9.1% S<br>11.4% N |
| 44 | $C_2H_5-$ | $n-C_4H_9NH-$ | $i-C_4H_9-$ | H | $CH_3-$ | O | 8.5% S<br>11.4% N | 8.7% S<br>11.4% N |
| 45 | $CH_3-$ | $i-C_3H_7NH-$ | $sec.C_4H_9-$ | H | $CH_3-$ | O | 8.6% S<br>12.7% N | 8.7% S<br>12.4% N |
| 46 | $CH_3-$ | $C_2H_5NH-$ | " | H | $CH_3-$ | O | 9.1% S<br>12.7% N | 9.4% S<br>12.9% N |
| 47 | $C_2H_5-$ | $i-C_3H_7NH-$ | " | H | $CH_3-$ | O | 10.1% S<br>11.5% N | 9.9% S<br>11.9% N |

-continued

| Example No. | R | R₁ | R₂ | R₃ | R₄ | X | Analysis found | calculated |
|---|---|---|---|---|---|---|---|---|
| 48 | $C_2H_5-$ | $n-C_3H_7NH-$ | " | H | $CH_3-$ | O | 8.9% S  11.6% N | 9.1% S  11.9% N |
| 49 | $C_2H_5-$ | $i-C_4H_9NH-$ | " | H | $CH_3-$ | O | 9.3% S  11.1% N | 9.1% S  11.4% N |
| 50 | $i-C_4H_9-$ | $CH_3NH-$ | " | H | $CH_3-$ | O | 8.5% S  11.5% N | 8.7% S  11.9% N |
| 51 | $C_2H_5-$ | $i-C_3H_7NH-$ | $i-C_3H_7-$ | H | $C_2H_5-$ | O | 8.9% S  11.6% N | 9.1% S  11.9% N |
| 52 | $C_2H_5-$ | $CH_3NH-$ | $i-C_3H_7-$ | H | $C_2H_5-$ | O | 9.2% S  12.5% N | 9.1% S  12.9% N |
| 53 | $C_2H_5-$ | $C_2H_5O-$ | $i-C_3H_7-$ | H | $C_2H_5-$ | O | 9.7% S  7.6% N | 9.9% S  7.9% N |
| 54 | $CH_3-$ | $i-C_3H_7NH-$ | $C_2H_5-$ | H | $CH_3OCH_2$ | O | 18.2% S  11.9% N | 18.0% S  12.3% N |
| 55 | $C_2H_5-$ | $CH_3NH-$ | $C_2H_5-$ | H | " | O | 9.1% S  12.6% N | 9.4% S  12.8% N |
| 56 | $C_2H_5-$ | $C_2H_5NH-$ | $C_2H_5-$ | H | $CH_3OCH_2-$ | O | 9.9% S  11.8% N | 9.8% S  12.3% N |
| 57 | $C_2H_5-$ | $n-C_2H_7NH-$ | $C_2H_5-$ | H | $CH_3OCH_2-$ | O | 9.6% S  11.6% N | 9.4% S  11.9% N |
| 58 | $C_2H_5-$ | $i-C_4H_9NH-$ | $C_2H_5-$ | H | $CH_3OCH_2-$ | O | 9.2% S  11.1% N | 9.0% S  11.4% N |
| 59 | $i-C_4H_9-$ | $CH_3NH-$ | $C_2H_5-$ | H | $CH_3OCH_2-$ | O | 8.9% S  11.6% N | 8.7% S  11.8% N |
| 60 | " | $CH_3NH-$ | $C_2H_5-$ | H | $CH_3OCH_2-$ | S | 8.8% S  7.4% N | 9.0% S  7.8% N |
| 61 | " | $n-C_3H_7S-$ | $C_2H_5-$ | H | $CH_3OCH_2-$ | O | 17.6% S  7.4% N | 17.9% S  7.5% N |
| 62 | $CH_3-$ | $i-C_3H_7NH-$ | $n-C_3H_7-$ | H | $CH_3OCH_2-$ | O | 16.9% S  11.0% N | 17.2% S  11.4% N |
| 63 | $C_2H_5-$ | $CH_3NH-$ | " | H | $CH_3OCH_2-$ | O | 8.9% S  12.0% N | 8.7% S  12.3% N |
| 64 | $C_2H_5-$ | $C_2H_5NH-$ | " | H | $CH_3OCH_2-$ | O | 9.3% S  11.6% N | 9.4% S  11.8% N |
| 65 | $C_2H_5-$ | $n-C_3H_6NH-$ | " | H | $CH_3OCH_2-$ | O | 9.2% S  11.6% N | 9.0% S  11.4% H |
| 66 | $C_2H_5-$ | $i-C_3H_7NH-$ | " | H | $CH_3OCH_2-$ | O | 8.9% S  10.8% N | 8.7% S  11.0% N |
| 67 | $C_2H_5-$ | $CH_3NH-$ |  | H | $CH_3OCH_2-$ | O | 8.2% S  12.5% N | 8.4% S  12.5% N |
| 68 | $C_2H_5-$ | $n-C_3H_7NH-$ |  | H | $CH_3OCH_2-$ | O | 9.9% S  11.1% N | 9.5% S  11.5% N |
| 69 | $C_2H_5-$ | $C_2H_5O-$ | " | H | " | O | 8.5% S  7.8% N | 8.8% S  8.0% N |
| 70 | $C_2H_5-$ | $n-C_2H_7S-$ | " | H | " | O | 8.9% S  7.3% N | 9.1% S  7.3% N |
| 71 | $CH_3-$ | $i-C_3H_7NH-$ |  | H | $CH_3-$ | O | 16.9% S  11.3% N | 16.8% S  11.5% N |
| 72 | $C_2H_5-$ | $CH_3NH-$ | " | H | $CH_3-$ | O | 8.9% S  11.9% N | 8.8% S  12.0% N |
| 73 | $C_2H_5-$ | $C_2H_5NH-$ | " | H | $CH_3-$ | O | 9.3% S  11.1% N | 9.1% S  11.5% N |
| 74 | $C_2H_5-$ | $i-C_3H_7NH-$ | " | H | $CH_3-$ | O | 8.6% S  10.7% N | 8.8% S  11.1% N |
| 75 | $C_2H_5-$ | $C_2H_5O-$ | 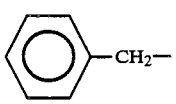 | H | $CH_3-$ | O | 8.1% S  7.9% N | 8.4% S  7.5% N |
| 76 | $C_2H_5-$ | $C_2H_5O-$ | " | H | $CH_3-$ | S | 8.7% S  7.5% N | 8.6% S  7.2% N |
| | | | | | | | 16.1% S | 16.4% S |

-continued

| Example No. | R | $R_1$ | $R_2$ | $R_3$ | $R_4$ | X | Analysis found | calculated |
|---|---|---|---|---|---|---|---|---|
| 77 | $C_2H_5$— | $C_2H_5O$— | 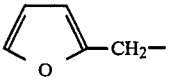 | H | $CH_3$— | S | 7.0% N<br>16.5% S | 7.4% N<br>16.8% S |
| 78 | $C_2H_5$— | $C_2H_5$— | " | H | $CH_3$— | S | 7.6% N<br>18.0% S | 8.0% N<br>18.3% S |
| 79 | $C_2H_5$— | n-$C_4$NH— | n-$C_2H_7$— | H | $CH_3OCH_2$— | O | 11.0% N<br>8.2% S | 11.0% N<br>8.4% S |
| 80 | $C_2H_5$ | $C_2H_5O$— | n-$C_2H_7$— | H | " | O | 8.1% N<br>8.8% S | 7.9% N<br>9.0% S |
| 81 | $C_2H_5$ | $C_2H_5O$— | n-$C_2H_7$— | H | " | S | 7.4% N<br>17.0% S | 7.5% N<br>17.2% S |
| 82 | $C_2H_5$ | n-$C_3H_7S$— | n-$C_2H_7$— | H | " | O | 7.5% N<br>16.8% S | 7.5% N<br>16.6% S |
| 83 | $CH_3$— | i-$C_3H_7$NH— | i-$C_3H_7$— | H | " | O | 11.8% N<br>8.8% S | 11.5% N<br>9.0% S |
| 84 | $C_2H_5$— | $CH_3$NH— | i-$C_3H_7$— | H | " | O | 11.9% N<br>9.1% S | 12.3% N<br>9.4% S |
| 85 | $C_2H_5$— | $C_2H_5O$— | i-$C_3H_7$— | H | " | O | 8.0% N<br>9.1% S | 7.9% N<br>9.0% S |
| 86 | $C_2H_5$— | n-$C_3H_7S$— | i-$C_3H_7$— | H | H | O | 7.4% N<br>16.2% S | 7.3% N<br>16.6% S |
| 87 | $CH_3$— | i-$C_3H_7$NH— | n-$C_4H_9$— | H | " | O | 10.7% N<br>8.8% S | 11.4% N<br>8.7% S |
| 88 | $C_2H_5$— | $CH_3$NH— | n-$C_4H_9$— | H | " | O | 11.6% N<br>9.3% S | 11.8% N<br>9.0% S |
| 89 | $C_2H_5$— | $C_2H_5O$— | n-$C_4H_9$— | H | " | O | 7.6% N<br>8.5% S | 7.6% N<br>8.7% S |
| 90 | $C_2H_5$— | n-$C_3H_7S$— | n-$C_4H_9$— | H | H | O | 7.4% N<br>15.8% S | 7.0% N<br>16.0% S |
| 91 | $CH_3$— | i-$C_3H_7$NH— | sec.-$C_4H_9$— | H | H | O | 11.7% N<br>8.8% S | 11.4% N<br>8.7% S |
| 92 | $C_2H_5$— | $C_2H_5O$— | " | H | H | O | 7.7% N<br>8.5% S | 7.6% N<br>8.7% S |
| 93 | $C_2H_5$— | n-$C_3H_7S$ | " | H | H | O | 7.4% N<br>16.8% S | 7.3% N<br>16.6% S |
| 94 | $C_2H_5$— | $CH_3$NH— | i-$C_3H_7$— | H | $CH_3SCH_2$— | O | 12.1% N<br>17.6% S | 11.8% N<br>17.9% S |
| 95 | $C_2H_5$— | $CH_3$NH— | n-$C_3H_7$— | H | 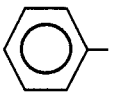 | O | 11.4% N<br>8.6% S | 11.8% N<br>8.9% S |
| 96 | $C_2H_5$— | n-$C_3H_7$NH— | n-$C_3H_7$— | H | " | O | 10.4% N<br>8.2% S | 10.5% N<br>8.0% S |
| 97 | $C_2H_5$— | $C_2H_5O$— | n-$C_3H_7$— | H | " | O | 7.3% N<br>15.6% S | 6.9% N<br>15.8% S |

(B) FORMULATION EXAMPLES

Example A

An emulsifiable concentrate is obtained from 15 parts by weight of active compound of the formula I, 75 parts by weight of cyclohexanone, as the solvent, and 10 parts by weight of nonylphenol polyglycol ether (10 AeO)+) as the emulsifier.

+)=number of ethylene oxide units in the polyglycol ether radical

Example B

A wettable powder which is readily dispersible in water is obtained by mixing 25 parts by weight of active compound of the formula I, 64 parts by weight of kaolin-containing quartz, as the inert substance, and 1 part by weight of sodium oleylmethyl-taurate, as the wetting and dispersing agent, and grinding the mixture in a pinned disc mill.

Example C

A dusting agent is obtained by mixing 10 parts by weight of active compound of the formula I and 90 parts by weight of talc, as the inert substance, and comminuting the mixture in an impact mill.

Example D

Granules are obtained by granulating a mixture of 2-15 parts by weight of active compound of the formula I and 98-85 parts by weight of an inert granule-carrier material, for example attapulgite, pumice granules, quartz sand, which contains a binder, if appropriate.

(C) BIOLOGICAL EXAMPLES

Example I

Bean plants (*Phaseolus vulgaris*) heavily infested with the two-spotted spider mite (*Tetranychus urticae*, normally sensitive) were sprayed with an aqueous dilution of a wettable powder concentrate containing 0.025% by weight of the active compound from Example 1, until the stage where the dilution starts to drip off. At the microscopic control eight days after the treatment, it was found that all the mobile and immobile stages of the population had been destroyed.

The compounds according to Examples 2, 3, 4, 7, 8, 11, 12, 13, 14, 15, 16, 17, 18, 19, 20, 24, 25, 26, 27, 28, 29, 30, 33, 34, 35, 36, 40, 41, 45, 46, 47, 52, 53, 54, 55, 56, 59, 60, 61, 62, 63, 69, 70, 76, 78, 80, 81, 82, 83, 84, 85, 86, 87, 90, 91, 92 and 93 proved to be just as effective when tested in the same manner.

Example II

Broad beans (*Vicia faba*) heavily infested with cowpea aphids (*Aphis craccivora*) were sprayed with an aqueous suspension of a wettable powder concentrate containing 0.0125% by weight of the active compound from Example 2, until the stage where the suspension dripped off. After the plants had been planted in a greenhouse, 100% destruction of the test animals was found three days after the treatment. The compounds according to Examples 3, 7, 8, 11, 12, 14, 15, 17, 24, 25, 27, 33, 34, 36, 40, 41, 45, 46, 47, 50, 55, 56, 57, 59, 60, 61, 62, 63, 69, 75, 77, 78, 80, 81, 82, 83, 84, 85, 86, 87, 88, 89, 91, 92 and 93 proved to be just as effective.

Example III

Potted broad beans (*Vicia faba*) the root balls of which were enveloped in foil, were treated, after being infected with two-spotted spider mites (*Tetranychus urticae*), with the compound to be tested by uniformly distributing an aqueous dilution of an emulsion concentrate (0.5 mg of active compound) in the region of the roots by means of a glass funnel. 8 days after the treatment, 100% mortality was achieved with the compounds according to Examples 7, 11, 13, 14, 15, 17, 18, 24, 25, 26, 27, 28, 30, 34, 45, 46, 50, 52, 53, 54, 55, 59, 60, 61, 62, 78, 80, 82, 83, 84, 85, 86, 91 and 92.

Example IV

Potted broad beans (*Vicia faba*), the root balls of which were enveloped in foil, were infected with the aphid *Aphis craccivora* and treated with the compound to be tested by uniformly distributing an aqueous dilution of an emulsion concentrate (1 mg of active compound) in the region of the roots by means of a glass funnel.

8 days after the treatment, 100% mortality was achieved with the compounds according to Examples 2, 3, 8, 11, 14, 15, 17, 24, 34, 40, 45, 46, 55, 59, 60, 69, 75, 77, 78, 80, 84, 85, 88, 89 and 92.

Example V

A dust-like formulation was mixed with earth infested with *Meloidogyne incognita*. The soil was then filled into pots and these pots were planted with tomatoes. After the plants had stood in a greenhouse for 4 weeks, the rating figures were determined in accordance with the following plan:

| Galls/plant | Rating |
|---|---|
| 0 | 1 |
| 1–2 | 2 |
| 3–5 | 3 |
| 6–10 | 4 |
| . | . |
| . | . |
| . | . |
| over 150 | 9 |

When an amount of active compound corresponding to an amount applied to 20 kg of active compound/ha was mixed in with the soil, the compounds according to Examples 1, 3, 7, 8, 13, 15, 17, 18, 19, 20, 26, 27, 28, 30, 34, 35, 37, 41, 44, 45, 46, 47, 51 and 83 achieved the rating 1.

Example VI 1 ml of Example 12, as the active compound, in acetone in a concentration of 0.025% by weight was applied uniformly to the inside of the lid and of the bottom of a Petri dish by means of a pipette, and the dish was left open until the solvent had evaporated completely. 10 house flies (*Musca domestica*) were placed in each Petri dish, the dishes were closed with a lid and, after 3 hours, 100% destruction of the test animals was observed. The compounds according to Examples 17, 24, 41, 61, 82, 86 and 90 proved to be just as effective.

Example VII

The compound according to Example 7, as the active compound, in acetone in a concentration of 0.025% by weight was applied uniformly to the inside of the lid and of the bottom of a Petri dish and the dish was left to dry, as described in Example VI. 10 larvae (L 4) of the German cockroach (*Blatella germanica*) were then placed into each Petri dish, the dishes were covered with the lid and, after 72 hours, 100% destruction of the test animals was found. The compounds according to Examples 8, 12, 17, 24, 41, 46, 53, 61, 82, 86, 90 and 93 proved to be just as effective.

Example VIII

Cotton leaves (*Gossypium sp.*) were sprayed with an aqueous emulsion of the compound according to Example 12 in a concentration of 0.05% by weight, based on the active compound, (=600 liters of spray liquor/ha) and caterpillars (10 specimens, stage L 3–4) of the cotton worm (*Prodenia litura*) which had been treated likewise were added. The leaves and caterpillars were placed in observation cages and, after 48 hours, 100% destruction of the test animals was observed. The compounds according to Examples 17, 24, 41, 61, 82, 89, 90 and 93 proved to be just as effective.

Example IX

Bean leaves (*Phaseolus vulgaris*) were treated with an aqueous emulsion of the compound from Example 3 in a concentration of 0.025% by weight (based on the active compound) and were given to similarly treated larvae of the Mexican bean beetle (*Epilachna varivestis*) in observation cages. Evaluation after 48 hours showed 100% destruction of the test animals. The compounds according to Examples 8, 17, 25, 33, 34, 41, 50, 53, 61, 62, 78, 82, 85, 90, 92 and 93 proved to be similarly effective.

We claim:

1. A compound of the formula I:

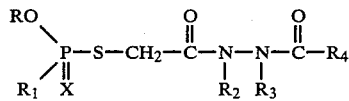

in which
R is $(C_1–C_4)$-alkyl,
$R_1$ is $(C_1–C_4)$-alkylamino or di$(C_1–C_4$-alkyl)-amino,
$R_2$ is $(C_1–C_4)$-alkyl,
$R_3$ is H, $(C_1–C_4)$-alkyl, $(C_5–C_6)$-cycloalkyl, benzyl or furylmethyl,
$R_4$ is $(C_1–C_4)$-alkyl, and X is oxygen or sulfur.

2. A method for combating harmful insects, acarides or nematodes which comprises applying an effective amount of a compound of claim 1 to the infested plants.

3. A method for combating nematodes which comprises applying an effective amount of a compound of claim 1 to the infested plants.

4. The compound as claimed in claim 1, in which $R_1$ is $(C_1-C_4)$-alkylamino, $R_3$ is H and $R_4$ is $CH_3$.

5. The compound as claimed in claim 1, in which $R_1$ is $(C_1-C_4)$-alkylamino, $R_3$ is hydrogen, $R_4$ is $CH_3$, and X is oxygen.

6. The compound N-(O-methyl-N-isopropylamidothiolophosphorylacetyl)-N-isopropyl-N'-acetylhydrazine.

7. The compound N-(O-ethyl-N-isopropylamidothiolophosphorylacetyl)-N-isopropyl-N'-acetylhydrazine.

8. The compound N-(O-methyl-N-isopropylamidothiolophosphorylacetyl)-N-sec.-butyl-N'-acetylhydrazine.

9. An insecticidal, acaricidal or nematocidal agent comprising an effective insecticidal, acaricidal or nematocidal amount of a compound of claim 1 in combination with a formulation auxiliary.

10. A nematocidal agent comprising an effective nematocidal amount of a compound of claim 1 in combination with an inert carrier.

* * * * *